Figure 1:
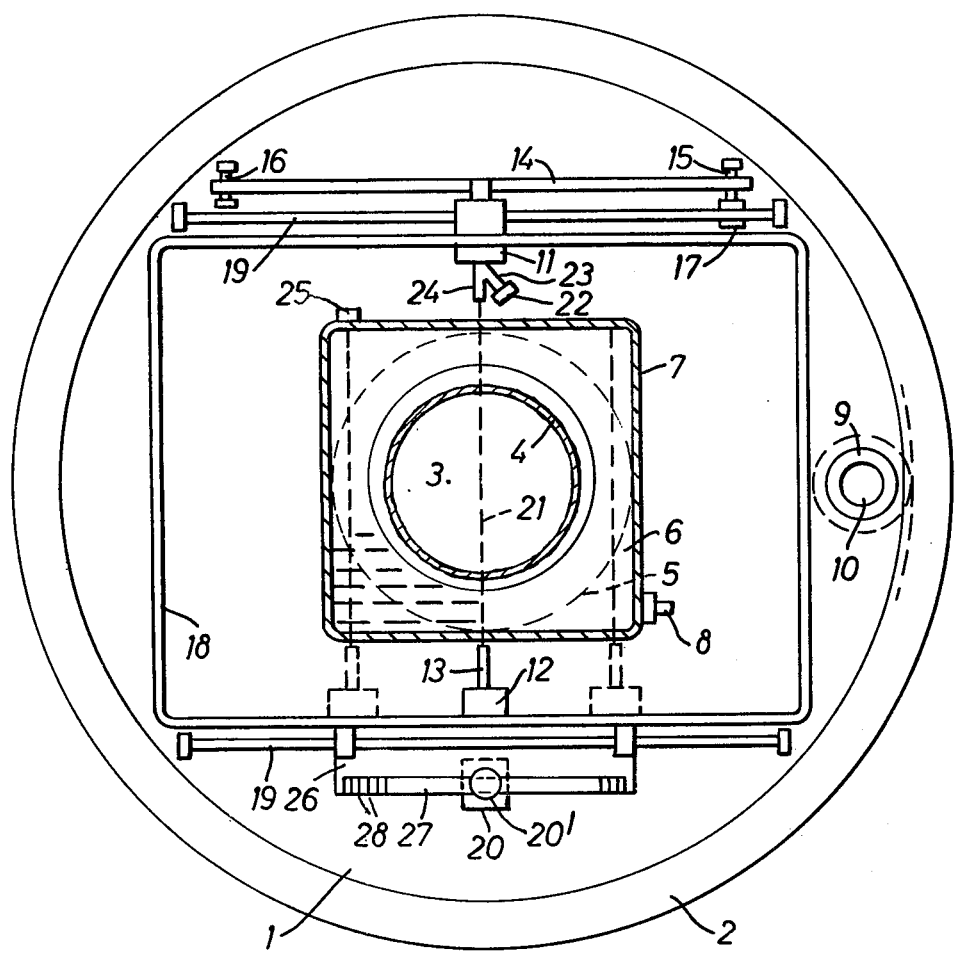

United States Patent [19]

Mayo et al.

[11] 4,032,761

[45] June 28, 1977

[54] TOMOGRAPHY

[75] Inventors: Bernard Joseph Mayo, Beaconsfield; John Edward Best, South Stoke, near Reading, both of England

[73] Assignee: E M I Limited, Hayes, England

[22] Filed: Oct. 9, 1975

[21] Appl. No.: 621,027

[30] Foreign Application Priority Data

Oct. 11, 1974 United Kingdom ............ 44049/74
Nov. 23, 1974 United Kingdom ............ 50840/74

[52] U.S. Cl. ........................... 235/151.3; 128/2 A; 250/445 R

[51] Int. Cl.² ................................... G03B 41/16

[58] Field of Search ............ 235/151.3; 250/445 R, 250/445 T, 369, 360, 362, 363, 446–450; 128/2 A

[56] References Cited

UNITED STATES PATENTS

| | | | |
|---|---|---|---|
| 3,778,614 | 12/1973 | Hounsfield | 250/445 T |
| 3,784,820 | 1/1974 | Miraldi | 250/362 |
| 3,852,603 | 12/1974 | Muehllehner | 250/369 |
| 3,875,412 | 4/1975 | Hozumi | 250/446 |
| 3,919,552 | 11/1975 | Hounsfield | 250/445 T |
| 3,924,131 | 12/1975 | Hounsfield | 250/445 T |
| 3,934,142 | 1/1976 | Hounsfield | 250/445 T |
| 3,936,636 | 2/1976 | Percival | 250/369 |
| 3,996,467 | 12/1976 | Froggatt et al. | 250/445 T |

*Primary Examiner*—Malcolm A. Morrison
*Assistant Examiner*—Errol A. Krass
*Attorney, Agent, or Firm*—Fleit & Jacobson

[57] ABSTRACT

Computerized axial tomographic apparatus provides sets of "edge readings" which relate to the absorption suffered by penetrative radiation on traversing respective paths through a part of interest in a body, the various paths being coplanar. These edge readings are processed to permit the evaluation of the absorption coefficients at a plurality of locations distributed over the part of the body in the irradiated plane. In accordance with the invention the necessity for such processing to involve large scale multiplication is overcome by employing a processing technique which utilizes Walsh functions.

1 Claim, 5 Drawing Figures

TOMOGRAPHY

The present invention relates to a method of and apparatus for examining a body by means of radiation such as X- or γ- radiation. It has particular but not exclusive application in the field of medical examination.

The specification of British Pat. No. 1,283,915 discloses and claims a method of and an apparatus for examining a body by means of penetrating radiation, which is capable of evaluating the distribution of absorption coefficients, with respect to the radiation used, over a planar slice disposed cross sectionally in the body. To permit such evaluation, the radiation is transmitted through the body along many substantially co-planar paths, the plane of the paths being arranged to coincide with the plane of the slice in the body. Detector means is disposed on the side of the body remote from the source of the radiation, so that the overall absorption suffered by the radiation on traversing the individual paths can be determined. The radiation may be directed through the body along many sets of paths, the paths of each set being parallel, and each set of paths being disposed at a respective angular position relative to the body. The detector means performs a photon count for every path and processing means operates on the data thus derived to set up an image in two dimensional form that shows directly the desired distribution of absorption coefficients. The processing is carried out with reference to a Cartesian meshwork, notionally delineated in the aforementioned slice, as an iterative procedure.

The iterative procedure tends to be time consuming because many steps of multiplication have to be carried out. It is also not possible to produce a representation of only a small area of the slice (which may be the only area of interest) without first performing all the steps of processing necessary to produce a representation of the entire slice.

A form of processing is known, based on a convolution technique, in which this latter disadvantage can be overcome. Even so the use of many steps of multiplication remains. An object of the present invention is to overcome this difficulty.

According to the invention there is provided a method of operating on electrical output signals, indicative of the absorption of radiation on traversing each of a plurality of co-planar paths through a part of a body under examination to evaluate the absorption coefficient at each of a plurality of locations distributed over the part of said body intersected by said paths, adjacent locations being separated by a predetermined distance, including processing said output signals in conjunction with signals representative of Walsh functions extending up to a sequency of the order of a spatial frequency corresponding to said predetermined distance to provide data corresponding directly to said absorption coefficients. Preferably, said method involves the utilization, of signals representative of Walsh transforms of the said output signals when these transforms have been multiplied in each case by a function of sequency to render them suitable for use as multiplying coefficients in an expansion representative of the distribution of said coefficients over said body part.

Figure 2:
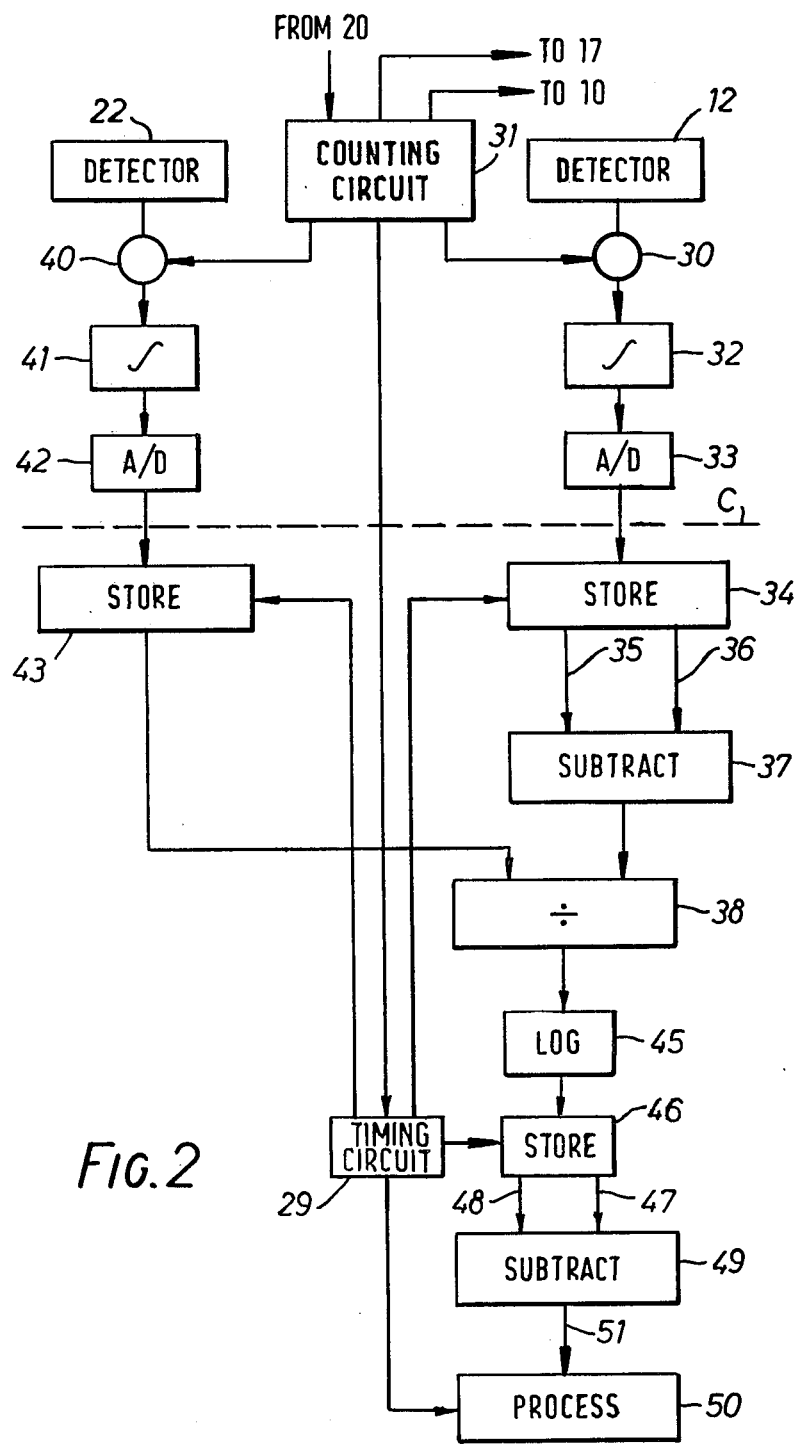
Figure 3:
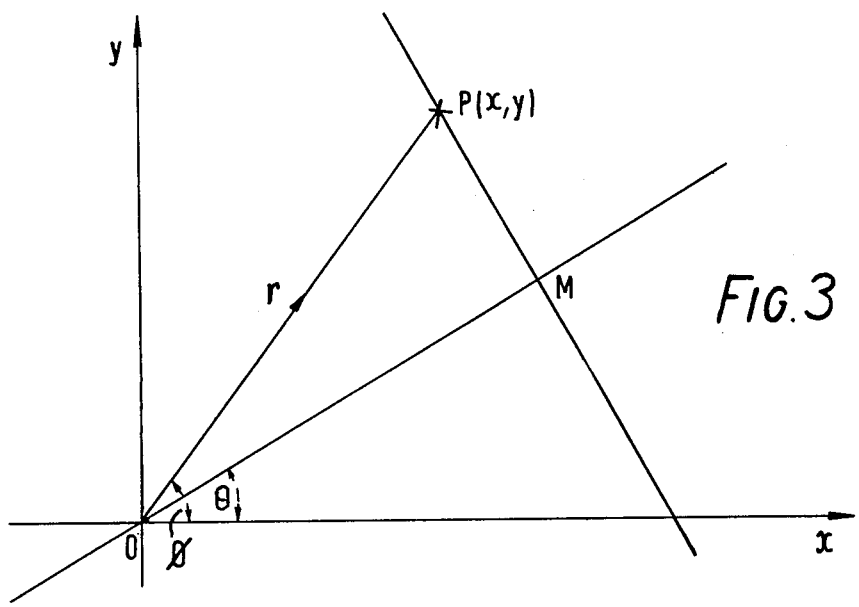
Figure 4:
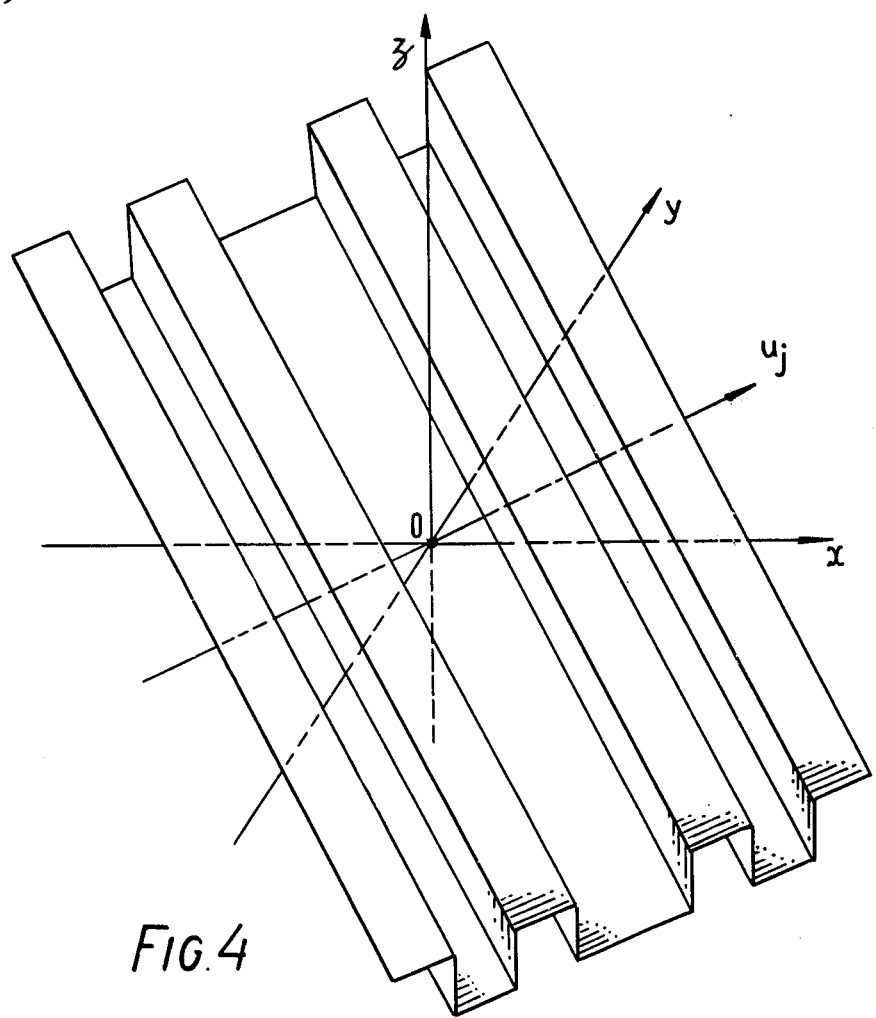
Figure 5:
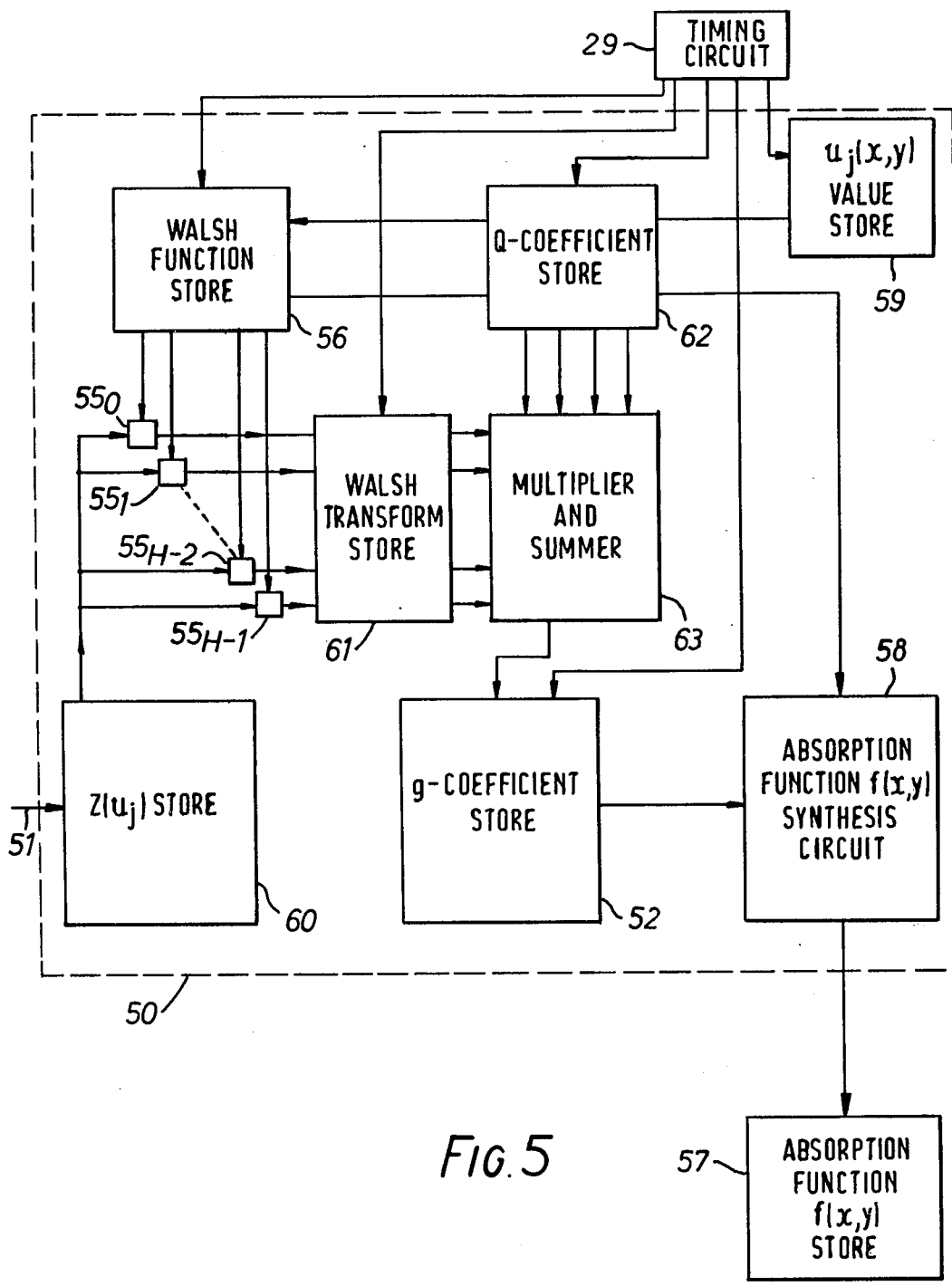

In order that the invention may be clearly understood and readily carried into effect, examples thereof will now be described with reference to the accompanying drawings in which:

FIG. 1 shows diagrammatically the scanning mechanism of an apparatus for examining a patient in accordance with one example of the present invention, FIG. 2 shows, in block diagrammatic form, a suitable circuit arrangement for use with the apparatus shown in FIG. 1, FIG. 3 is a graphical diagram relating to the plane of exploration of the body under examination, FIG. 4 shows a representation of a typical Walsh function as used in the processing and FIG. 5 shows, in block diagrammatic form, a processor unit employed in accordance with one example of the invention.

Referring to the drawings, the apparatus (which is in a form suitable for examination of the head of a patient) comprises a rotary member 1 which is rotatable inside a fixed casing 2 forming part of the main frame of the apparatus. The rotary member 1 has a central aperture 3 in which the head of the patient to be examined can be inserted. The central aperture is closed in a water-tight manner by a pouched cover 4 of flexible material which is secured to a sealing flange 5. This flange is held in sealing, but rotatable, relationship with the remote face of the member 1. The pouch is shown in section in FIG. 1. The head of the patient is inserted through the aperture 3 into the pouch of the cover 4, and an additional head rest, not shown, may be provided to support the head in the pouch. A suitable chair or bed is provided to support the patient during the examination. When the head is inserted through the aperture 3 into the pouch 4 it projects into a water reservoir 6 having side walls 7, the pouch separating the head from the water. The reservoir is closed at the front by the member 1 and cover 4, at the side by the walls 7 which are made of plastic, and at the rear by a base wall, not shown. The walls 7 and the base wall rotate with the member 1, whereas the cover 4, with its flange 5, remains stationary, the flange being secured to the frame of the apparatus. A pipe 8 is connected to a pump for feeding water to and from the reservoir and after the patient's head has been inserted in the pouch, water is pumped into the reservoir 6 so as to expel the air from between the pouch and the patient's head.

A tooth-geared wheel 9, driven by a motor 10 is provided for driving the rotatable member 1 so as to produce orbital scanning of the member 1 about its axis, which is also the axis of the aperture 3. The gearwheel 9 engages teeth formed around the inner periphery of the casing member 2. The rotatable member carries a source 11 of penetrating radiation, an X-ray generating tube in this example, and facing the source 11, on the other side of the aperture 3 there is provided an X-ray detector 12. The detector 12, which comprises a scintillation crystal and a photomultiplier, has a collimator 13. The source of radiation 11 is arranged to be an effective point source and it has a collimator 24, the collimators 13 and 24 confining the radiation reaching the detector 12 to a single narrow beam 21 lying in a plane section normal to the axis of the rotary member 1. The plane lies within the reservoir 6.

The source 11 is secured to a toothed belt 14 driven by a toothed drive shaft 15 journalled in the rotatable member 1, the belt being extended between the shaft 15 and the second shaft 16 also journalled in the member 1. The shaft 15 is driven by a reversible motor 17, the controls of which are interlocked with those of the motor 10. Since the source 11 is massive, a counter balance weight, not shown, is provided secured to the other run of the belt so as to move reciprocally with the source. In operation of the apparatus, the source 11 and the collimator 24 are caused by the motor 17 to execute to and fro lateral scanning movements in the aforementioned plane normal to the axis of the rotary member 1. The detector 12 and the collimator 13 are coupled to the source 11 by a yoke 18 so that they execute the same lateral scanning movements. Guides 19 are provided to support the source and the yoke during the lateral scanning. Output signals are derived from the detector 12 during each lateral scan and those signals represent the transmission or absorption of the beam 21 along a set of closely spaced, parallel paths in the planar section under examination.

The interlock between the motors 10 and 17 is such that following each lateral scan, in either direction, an increment of orbital movement of say 1° is imparted to the rotary member 1 by the motor 10. Thereafter another lateral scan occurs under the control of the motor 17 but this time in the reverse direction to the preceding lateral scan. A further set of output signals, representing the transmission of the beam 21 along a further set of closely spaced, parallel paths, is derived, this set of beam paths being orientated at 1° relative to the preceding set. A photocell device, comprising a photosensitive cell 20 and a suitable light source 20', and a transparent graticule 27, coupled to the yoke 18 by a supporting plate 26 and carrying equally spaced opaque markings as shown at 28, are arranged to cooperate in known manner to monitor the lateral scanning displacements and determine the timing of the output signals. The alternate orbital end lateral scanning movements are continued until a total orbital movement of about 180° has been completed.

As indicated in FIG. 1, the reservoir 6 has a lateral extent substantially equal to that of the lateral scan, the extremities of which are indicated by the dotted beams (other than beam 21). It projects to either side of the aperture 3 so that at the beginning of each lateral scan the beam 21 is for a time traversing a known path length through the water in the reservoir. The reservoir, when filled with water, thus provides a reference attenuator so positioned relative to said locating means as to provide a known attenuation of the beam 21 whilst the beam is outside the region 3 in which the body is located. As will appear subsequently, a reference signal is derived from the detecting means while the beam is intercepted by the water reservoir and this reference signal is utilized for modifying output signals derived when the beam is intercepted by the body to be examined to take account of variations in the performance of the detector 12 during the examination. As the walls of the reservoir other than the cover 4, rotate with the member 1, the path of the beam through the reference attenuator provided by the side portions of the reservoir 6 is substantially the same for every lateral scan regardless of the angular orientation. There is also provided mounted on the member 1 a block of lead 25 which is located at one extremity of the lateral scans carried out by the source 11 and detector 12. The lead block 25 provides substantial absorption of the X-radiation and the output signal from the detector 12 when the beam is intercepted by the lead provides a second reference signal which is utilized to modify the signals derived from the detector to allow for "after glow" in the detector 12 not only when the beam 21 is intercepted by the body to be examined, but also when it is intercepted by the parts of the reservoir which act as reference attenuators. It is to be noted that the reservoir 6 provides attenuation of the beam 21 throughout the lateral scanning movements, but the attenuation is reduced in the regions where the beam is liable to be intercepted by the body to be examined. Since the attenuation of water is close to that of human tissue, the effect is to reduce substantially variations in the absorption of the beam during scanning, except when the beam is intercepted by the lead block 25. In the circuit for processing the output signals of the detector 12, the reference signal derived when the beam suffers the known attenuation through water at the beginning of each lateral scan is subtracted from the other output signals, and the resultant output signals represent substantially only differences in the attenuation of the beams within the body examined from that of transmission through water.

A reference detector 22 is mounted close to the X-ray source 11 so that it received radiation directly from the source via a collimator 23. The detector 22 is provided to monitor the energy of the X-rays.

The block diagrammatic circuit shown in FIG. 2 commences with the detectors 12 and 22 of the apparatus that has been described with reference to FIG. 1. The output signals of the detector 12 are applied to a gate 30 which is opened at predetermined times by sampling pulses derived from a master counting circuit 31. This master counting circuit receives input signals from the photocell device 20, which signals are in the form of pulses, one for each beam path, derived as the graticule 27 moves relative to the photocell device 20, 20'. If there are $n$ parallel paths in a set, then the photocell device 20, 20' is arranged to produce $n$ pulses during a single lateral scan of the source 11 and the detector 12 relative to the body. The master counting circuit 31 thus comprises an $n$ position ring counter, which is arranged to supply suitable control signals not only to the gate 30 but also the motor 10 and to the reversing motor 17. These last mentioned control signals are supplied each time the counter 31 has counted $n$ pulses. The sampling pulses supplied by the circuit 31 to the gate 30 are produced at times determined by the aforesaid graticule 27 so as to derive from the detector 12 a succession of output signals corresponding to the transmission of the beam 21 through a set of parallel paths, as already indicated. The orientation for the set of paths is determined by the angular position of the rotatable member 1, and if desired a further counter (not shown) may be provided to count the control pulses fed to the motors 10, 17 thereby to maintain a count of the number of increments of angular rotation which have been performed at any given time. During each sampling interval, the output of the detector 12 is integrated in an integrator 32 and then converted to digital code form in an analogue-to-digital converter 33.

The signal generated during each sampling pulse is stored, in digital form, in a respective storage location of a digital store 34. The storing of such signals is effected under the control of a timing circuit 29, which itself receives information relating to the progress of the scanning from the counting circuit 31.

As will be appreciated from the preceding description of FIG. 1, the X-ray beam 21 is intercepted by the lead block 25 once in every two lateral scans and therefore the corresponding output signal from the detector 12 is stored, in store 34, for the duration of two lateral scans. The signals stored in store 34 which relate to a particular set of parallel paths include those obtained when the X-ray beam 21 is known to pass through the reference paths in the reservoir 6 and those obtained when passing through the body under examination. The output signal derived from the detector at the time when the beam 21 was substantially interrupted by the lead block 25 is read out repeatedly, under the control of circuit 29 and applied to a subtracting circuit 37 by way of a conductor 35. Signals derived at other times during a traverse are read out in sequence, again under the control of circuit 29, and applied to circuit 37 by way of a conductor 36. The arrangement is such that the reference signal representing the virtually complete attenuation introduced by the lead (i.e. the one repeatedly read out on conductor 35) is substracted from each other signal of a sampling set, so that after the subtraction the resulting signals represent the transmission or absorption of the beam 21 within the examined body related to the absorption of lead as a datum. In this way the effect of 'after glow' in the detector 12 is largely removed. The resulting signals are passed into a dividing circuit 38.

The reference detector 22 previously referred to has an output gate 40 which receives sampling pulses from counting circuit 31, coincident with the sampling pulses applied to the gate 30. Signals passing through the gate 40 are integrated in an integrator 41 and converted to digital form in a converter 42, these components 41 and 42 corresponding to the integrator 32 and converter 33. The digitised signals from the detector 22 are then passed to a store 43 where they are stored in respective locations under the control of circuit 29. The stored signals are derived from store 43, again under the control of circuit 29, and are applied with appropriate timing to the aforesaid dividing circuit 38.

In the dividing circuit each signal derived from the detector 12 is divided by the corresponding signal contemporaneously derived from the detector 22 to compensate for variations in energy of the source 11. The signals so compensated are passed to a log converting circuit 45 which translates each signal applied thereto into its logarithm and the signals thus translated are stored, in this form, in respective storage locations of another store 46, which is also operated under the control of circuit 29. These signals are applied, again under the control of timing circuit 29, by way of one of two conductors 47 or 48 to a substracting circuit 49. The conductor 47 is arranged to carry signals relating to periods when the X-ray beam 21, during any particular traverse, passed through the region in which the body to be examined may be located, while the conductor 48 is arranged to carry signals relating to periods when the beam 21 passed through the reference paths in the water and was therefore subjected to a known attenuation. The signals on the conductor 47 may therefore be termed reference signals, those on the conductor 48 being distinguished as output signals. The reference signal moreover is read out repeatedly to coincide with each output signal of a particular scan and it is subtracted in subtraction circuit 49 from these output signals so that the output signals then represent only the difference in the attenuation of the beam 21 from the known attenuation produced by the water in the reservoir. The output signals after these modifications are fed to a signal processor 50 to participate, along with the output signals of all the other sets, in the image reconstruction of the distribution of absorption of the exploring radiation in the section of the body under examination.

Many variations may be made in the form of the apparatus that has so far been described. For example, the attenuator formed by the reservoir of water may be replaced by an attenuator made of solid material such as plastic, suitably shaped to provide an equivalent effect to that produced by the water reservoir. In this case a locating collar may be provided for the body to be examined and a separate water jacket disposed between the collar and the body located in the collar. Several detectors such as 12, with appropriate collimators, may be provided to simultaneously receive several beams of radiation from the source 11. In this case the said beams may be inclined at small angles to each other. The total orbital scanning movement may moreover differ from 180°. There may, moreover, be two or more beams such as 21, one behind the other, so that two or more adjacent planes may be examined simultaneously.

In accordance with the invention, the processing unit 50 avoids the large scale of multiplication in the sequence of steps which it employs to evaluate the required absorption coefficients because the processing effected by the unit 50 is based on transformations of a kind known as Walsh transformations. In this kind of transformation while, as a purely formal matter, the sets of sampled absorption data become multiplied by processing functions in the unit 50, nevertheless, since these functions are so-called Walsh functions which assume only the values of +1 and −1, it follows that no actual steps of multiplication in the normal sense are necessary, and the transformations of processing reduce to a series of additions and subtractions.

The nature of the processing will now be explained in more detail, but first as an aid to this explanation a development of known Fourier methods of processing the data will be set out.

Suppose $f(x,y)$ to represent the distribution, in the plane of the Cartesian coordinates $x,y$, of the absorption per unit length of material in the plane with respect to a given radiation. There exists a Fourier transformation of the function $f(x,y)$ with regard to the variables $x$ and $y$ defined by $$F(a,b) = \int_{-\infty}^{+\infty} \int_{-\infty}^{+\infty} f(x,y) e^{-2\pi i(ax+by)} dx dy .$$

Assuming the transform function F($a,b$) is known, the absorption function $f(x,y)$ is given by the inverse transformation according to $$f(x,y) = \int_{-\infty}^{+\infty} \int_{-\infty}^{+\infty} F(a,b) e^{2\pi i(ax+by)} da db .$$

The variables $a$ and $b$ are those of the Fourier transform plane, and they may be considered as given by the equations $a = k \cos \theta$
$b = k \sin \theta .$ By virtue of these equations the index of the exponential factor may be represented simply as $2\pi i k u,$ if
$$u = x\cos\theta + y\sin\theta.$$
Thus, writing $$C(k,\theta) = F(a,b),$$

the absorption function may also be expressed in polar manner according to the Fourier transform relationship $$f(x,y) = \int_0^\pi \int_{-\infty}^{+\infty} C(k,\theta) e^{2\pi i k u} \cdot k\, dk\, d\theta.$$

Since $u$ is a function of $x$ and $y$ this shows that the absorption function may be regarded as the sum of the doubly infinite set of Fourier functions of which $$C(k,\theta) e^{2\pi i k u} k\, dk\, d\theta$$

is typical, the set being distributed over all values of $k$ between $-\infty$ and $+\infty$ and over all values of $\theta$ between 0 and $\pi$. The variable $k$ represents the Fourier function spatial frequency, and the character of such functions is made more clear by reference to FIG. 3.

In this FIGURE there are shown the axes of the absorption plane, $0x$ and $0y$, and $0M$ is a straight line drawn through the origin of cooridinates 0 at an angle $\theta$ with the $0x$ axis. The point P is a typical point in the plane and of coordinates x,y. The point M is the intercept on $0M$ of the normal PM to OM drawn through the point P. The distance of the intercept M from the origin O is equal to the magnitude $u$, since, if $r$ and $\phi$ are the polar coordinates of the point P with respect to the origin O and axis Ox, then $u$ is the length $r\cos(\phi-\theta)$ of the projection of OP on OM. It will thus be evident that the value of the set of functions defined by a given value of $\theta$ will be the same for all values of $x$ and $y$ corresponding to all points on the line PM. It will also be evident that there are as many distinguishable set functions as there are distinguishable pairs of values $k,\theta$ in the Fourier transform plane.

In this last regard a material limitation must be supposed to exist in the field of practice by reason of sampling limitations. Thus it must be supposed that the transform function $C(k,\theta)$ vanishes effectively for all values of $k$ greater than some limit value that is determined by the sampling. In regard to the absorption plane it is a necessary presupposition that $f(x,y)$ vanishes for all values of $u$ greater than some limit value, ½A say.

In the foregoing context the polar Fourier expression for the absorption function that has been set out may be replaced by a Walsh expansion, also polar in form, according to $$f(x,y) = \int_0^\pi \sum_{h=0}^{H-1} G(h,\theta)\, \text{wal}(h,\xi)\, d\theta,$$

in which $$G(h,\theta) = \int_{-\infty}^{+\infty} [\alpha(k,\theta)m(h,k) - \beta(k,\theta)n(h,k)]\, k\, dk$$

the variable $\xi$ being a normalised value of the variable $u$, according to
$$\xi = u/A,$$

the functions $\alpha$ and $\beta$ being the real and imaginary parts respectively of the transform function $C(k,\theta)$, and the functions $m$ and $n$ being Walsh expansion coefficients defined by $$m(h,k) = \int_{-\frac{1}{2}}^{+\frac{1}{2}} \cos 2\pi A k t \cdot \text{wal}(h,t)\, dt$$

$$n(h,k) = \int_{-\frac{1}{2}}^{+\frac{1}{2}} \sin 2\pi A k t \cdot \text{wal}(h,t)\, dt.$$

The symbol $h$ signifies the sequency of a Walsh function, and it is assumed that $h$ ranges over all values of the sequency from zero to an upper limit $H-1$. It is also assumed that the contemplated set of H Walsh functions is such that the functions of the set are orthogonal in the range of the normalised function variable specified as $(-½, ½)$.

It can be shown that the coefficients, of which $G(h,\theta)$ is typical, of the Walsh expansion for $f(x,y)$ may be expressed according to $$G(h,\theta) = \sum_{h'=0}^{H-1} Q(h,h')\omega(h',\theta),$$

where $$\omega(h',\theta) = \int_{-\infty}^{+\infty} Z(\xi,\theta)\, \text{wal}(h',\xi)\, d\xi,$$

in which $Z(\xi,\theta)$ is the line integral $$\int_{-\infty}^{+\infty} f(x,y)\, dv$$

taken along PM in FIG. 3, and where $$Q(h,h') = \int_{-\infty}^{+\infty} q(h,h',k)\, dk,$$

given that $$q(h,h',k) = k m(h,k) m(h',k) + k n(h,k) n(h',k).$$

Thus the coefficient $G(h,\theta)$ is given on these lines as the series $$Q(h,0) \int_{-\infty}^{+\infty} Z(\xi,\theta)\, \text{wal}(0,\xi)\, d\xi$$

$$+ Q(h,1) \int_{-\infty}^{+\infty} Z(\xi,\theta)\, \text{wal}(1,\xi)\, d\xi$$

$$+ Q(h,2) \int_{-\infty}^{+\infty} Z(\xi,\theta)\, \text{wal}(2,\xi)\, d\xi$$

$$+ Q(h,3) \int_{-\infty}^{+\infty} Z(\xi,\theta)\, \text{wal}(3,\xi)\, d\xi$$

$$+ \ldots$$

When the coefficients such as $G(h,\theta)$ are so chosen, then the absorption function $f(x,y)$ can be evaluated, using the coefficients in the Walsh expansion for $f(x,y)$, so that the absorption image as given by $f(x,y)$ is free of frequency emphasis. If, however, a frequency emphasis, expressible as $\phi(k)$, is required, then $\phi(k)$ must be included as a multiplying factor in the right hand side of the expression given above for $q(h,h',k)$.

The Walsh expansion for $f(x,y)$ may be expressed in fully discrete form by replacing the integration with respect to $\theta$ by summation over a set of angles, J in number, of which $\theta_j$ is one angle of the set, the angular interval having the small value $\Delta\theta$. Then writing $$G(h,\theta_j) \cdot \Delta\theta = g(h,j)$$

the expression becomes $$f(x,y) = \sum_{x=0}^{J-1} \sum_{h=0}^{H-1} g(h,j) \, \text{wal}\,(h,\xi) \,;$$

or $$f(x,y) = \sum_{j=0}^{J-1} \sum_{h=0}^{H-1} g(h,j) \, \text{wal}\,(h,u_j) \,,$$

if $u_j$ is written in place of the variable $\xi$, using the suffix $j$ to indicate that the variable is understood to relate to the $j$th angular direction.

The expansion in the form thus set out sums a double set of Walsh functions, the set being double in the sense that it may be regarded as a set of sub-sets each member of the latter being associated with a different value of the direction parameter $j$, and each sub-set being formed of a set of Walsh functions of sequency ranging from 0 to H−1. FIG. 4 shows a typical Walsh function of the sub-set associated with the direction parameter $j$, the function being represented pictorically as a surface function, namely as ordinate values, $z$, normal to the $x,y$ plane. With each surface function there is an associated coefficient $g(h,j)$, as has been stated, and with the association of these coefficients the expansion for $f(x,y)$ gives $f(x,y)$ at each point $(x,y)$ as an ordinate equal to the sum of the ordinates of all the surface functions at the point in question. In the direction of each direction parameter value, $j$, the Walsh functions do not need to be regarded as extending beyond the bounds of the normalised variable $u_j$, that is to say beyond the bounds ±½.

It is to be noted that the Walsh functions, although differing in form from the Fourier functions, classify like Fourier functions into two sets, all members of one set being processed of strict symmetry about the variable origin, all those of the other set being strictly anti-symmetrical in regard to the origin. The symmetrical Walsh functions, the "cal" functions, correspond to the cosine functions of Fourier analysis, while the anti-symmetrical Walsh "sal" functions correspond to the sine functions. The "sequency" of Walsh functions moreover corresponds to the frequency of Fourier functions.

In the light of the foregoing theoretical considerations the nature and manner of operation of the processor unit 50 as shown in FIG. 2 will now be described with reference to FIG. 5. The unit 50 receives control signals from the timing circuit 29 and this latter unit is accordingly included in FIG. 5.

In this latter FIGURE conductor 51 represents the conductor which in FIG. 2 performs the function of conveying beam absorption signals from the subtracting circuit 49 to the unit 50. The signals conveyed are representative in sets, that is to say in dependence upon the angle parameter $j$, of the line integrals of absorption, earlier denoted typically as $Z(\xi,\theta)$ but in the discrete context of the FIGURE indicated therein typically by the notation $Z(u_j)$ in relation to a store 60 in which they are initially stored. According to the invention, and as part of a first step in the processor unit 50, the values of $Z(u_j)$ are withdrawn from store 60 and for each value of $j$ in turn the corresponding set of $Z(u_j)$ values is convolved with each of the Walsh functions, of the kind wal $(h,u_j)$, defined by setting $h=0,1,2,3\ldots$, H=1. Resulting from said first step of processing, and as will be explained in more detail, there are derived each of the HJ coefficients that may be set out as the array

| | | | |
|---|---|---|---|
| g(0,0) g(0,1) g(0,2) | ... | g(0,J−1) | |
| g(1,0) g(1,1) g(1,2) | ... | g(1,J−1) | |
| g(2,0) | | . | |
| . | | . | |
| . | | . | |
| . | | . | |
| g(H−1,0) | ... | g(H−1,J−1). | |

These coefficients as they are produced are stored in a "g-coefficient" store 52.

The convolutions referred to are performed by means of the multiplying circuits $55_0, 55_1, \ldots 55_{H-2}, 55_{H-1}$ to which (under control from the timing circuit 29) Walsh function values from a Walsh function store 56 are applied respectively in relation to Walsh function sequency order. Thus in relation to a multiplying circuit that may be designated typically $55_s$, values of the Walsh function wal $(s,u_j)$ are applied from the store 56 exclusively to this multiplier. More particularly when the Walsh function value wal $(s,u_j)$ is applied to multiplier $55_s$ then the absorption datum value $Z(u_j)$ drawn from the store 60 is also applied to this multiplier to be multiplied with the first value. Products as they are thus formed corresponding to the sequence of values assumed in turn by the variable $u_j$, and as dictated by the sampling process of absorption data acquisition, are passed to a Walsh transform store 61, where they accumulate to form the transform earilier denoted, in terms of continuous variable theory, after the fashion $$\int_{-\infty}^{+\infty} Z(\xi, \theta) \, \text{wal}\,(s,\xi) d\xi \,,$$

which may also be represented $$\int_{-\infty}^{+\infty} Z(u_j) \, \text{wal}\,(s,u_j) du_j \,.$$

As will be appreciated the transforms formed as described, of which the last expression is typically representative, total H in number, and all H transforms are stored in Walsh transform store 61.

In a Q-coefficient store 62 there are stored all the coefficients designated earlier in typical form by $Q(h,h')$. From these stored coefficients, and the transforms stored in store 61, the g-coefficients such as $g(h,j)$ are formed as the scalar products also set out earlier. Thus if $w_{sj}$ signifies the stored Walsh transform $$\int_{-\infty}^{+\infty} Z(u_j) \, \text{wal}(s, u_j) du_j ,$$

then the coefficient $g(h,j)$ is derived by forming the scalar product $$\sum_{s=0}^{H-1} Q(h,s) \cdot w_{sj}.$$

This scalar product is formed by withdrawing the appropriate Q-values from the Q-coefficient store 62, and the appropriate Walsh transform values from the Walsh transform store 61, under the control of timing circuit 29, and applying them to a multiplier and summer circuit 63 in which the multiplication and summation as required is performed to generate the value $g(h,j)$. With the generation of this value it is stored in the g-coefficient store 52.

Having derived the g-coefficient values to hold them in store 52, the further step of the processing unit 50 is to synthesize values of the absorption function $f(x,y)$ in accordance with the invention, as earlier explained, using the stored g-coefficients to this end. The synthesized values are transferred as they are generated to an image reconstruction store 57. This store holds values of the absorption function $f(x,y)$ as synthesized, relative to various mesh elements of a Cartesian meshwork that notionally extends over the plane of the explored cross-section of the examined body. The synthesis of the absorption function value is carried out by a synthesis circuit 58 under the control of unit 31. This is accomplished using on the one hand g-coefficient values drawn from store 52, and on the other Walsh function values taken from store 56 appropriate to the Cartesian meshwork coordinates, $x$ and $y$, relative to differing mesh elements to the notional meshwork relating to the image reconstruction store 57. Thus values of the beam absorption set variable represented generically by $u_j$ are stored in store 59 corresponding to these differing mesh elements. The store 59 is activated by control unit 31 to withdraw from the Walsh function store 56 values of all Walsh functions over the sequency range (O,H−1) relative to selected $x$, $y$ coordinates. These values are used in circuit 58 in conjunction with the withdrawn g-coefficient values to generate in turn values of the absorption function $f(x,y)$ appropriate to mesh elements of the notional meshwork of all or selected addresses in store 57. The synthesis as has been explained operates in accordance with the image function expansion $$f(x,y) = \sum_{j=0}^{J-1} \sum_{h=0}^{H-1} g(h,j) \, \text{wal}(h, u_j) .$$

Although this expression formally denotes multiplication of the g-coefficients by Walsh functions, since these functions can take only the values ±1 the multiplications reduce simply to the attaching of signs to the g-coefficients. Thus the synthesis in fact only entails algebraic summation, with corresponding brevity of processing time.

The value of the highest sequency employed, namely the value of H−1, is chosen so as to be of the order of the reciprocal of the sampling interval between the effective sampling beams of absorption value sets, and may be sensibly greater than this reciprocal value.

It will be realised that if the proper means value component of the image function is not required to be present in the final image reconstruction, then there is no need to evaluate any of the coefficients g(0,0), g(0,1) . . . g(0,J−1). If the mean value component is nevertheless required to be present, then as an alternative to the procedure described these coefficients need not be evaluated, but the proper mean value component may be inserted by arranging that in the extreme positions the exploring beams pass through a track of known overall absorption. In the final representation it is then only needed to ensure that an added uniform component of absorption is such that this known absorption is represented correctly.

While the processing as described with reference to FIG. 5 is of digital kind if, as is usually so, a high degree of accuracy is called for, in those circumstances where such accuracy is not material it is feasible to employ analogue methods of processing with certain economies, and in this event the storage of data is afforded by the use of storage tubes. In particular the data sequences summed in the Walsh transforms store 61 to form the Walsh transforms stored therein are summed in the process of writing the data into the storage provided by an appropriate storage tube serving the purpose of store 61. In particular also the synthesis pf the image function $f(x,y)$ in the snythesis circuit 58 is accomplished by the super-position in storage, as provided by a suitable storage tube, of the various Walsh surface functions, such as are illustrated in FIG. 4, employed in the synthesis. This storage tube then assumes also the function of the final image store 57.

What we claim is:

1. A method of operating on electrical signals, each indicative of a line integral of absorption suffered by penetrating radiation, on traversing a respective beam path through a slice disposed cross-sectionally of a body under examination so as to produce a representation of the absorption coefficient, with respect to said radiation, at each of a plurality of locations distributed over said slice; the beam paths comprising a set of substantially parallel paths at each of a plurality of angular orientations relative to the body; the method comprising the steps of:
   a. convolving the signals relating to a first set of said paths each with a plurality of values of Walsh functions of different sequency to produce a plurality of convolved signals of respective sequencies, each containing contributions from the signals relating to each beam path in said first set.
   b. forming the scalar product of each convolved signal with a respective series of coefficients each determined by a first sequency factor which is constant throughout the series and is of the same sequency as the relevant convolved signal and a second sequency factor which is different for each coefficient of the series,
   c. storing said scalar products in a coefficient store,
   d. repeating the method steps (a), (b) and (c) for the signals relating to the other sets of beam paths, and
   e. inverting the products stored in said coefficient store in dependence upon respective values of Walsh transform functions to evaluate said absorption coefficients.

* * * * *